United States Patent [19]

Venturello et al.

[11] Patent Number: 5,536,434

[45] Date of Patent: * Jul. 16, 1996

[54] IMIDO-DERIVATIVE PEROXYCARBOXYLIC ACIDS

[75] Inventors: Carlo Venturello, Novara; Claudio Cavallotti, Milan; Elena Bencini, Mantova; Maria A. Sasso, Chieri, all of Italy

[73] Assignee: Ausimont S.p.A., Italy

[*] Notice: The portion of the term of this patent subsequent to Jan. 19, 2019, has been disclaimed.

[21] Appl. No.: 425,292

[22] Filed: Oct. 20, 1989

[30] Foreign Application Priority Data

Oct. 24, 1988 [IT] Italy ........................... 22402/88

[51] Int. Cl.⁶ ................................. C07D 487/04
[52] U.S. Cl. .................. 510/375; 548/513; 548/547; 510/310; 510/500; 510/305; 510/307; 252/186.42
[58] Field of Search .................... 548/513, 547, 548/473, 479; 252/95

[56] References Cited

FOREIGN PATENT DOCUMENTS

| | | |
|---|---|---|
| 349940 | 7/1989 | European Pat. Off. . |
| 3823172 | 1/1990 | Germany . |
| 90/07501 | 7/1990 | WIPO . |

OTHER PUBLICATIONS

H. Gethoeffer et al., Chem. Abst. vol. 113: 58931X (1990).
C. Venturello et al., Chem. Abst. vol. 112: 80000u (1989).
C. Venturello et al., Chem. Abst. vol. 112: 76941j (1989).

*Primary Examiner*—Nicholas Rizzo
*Attorney, Agent, or Firm*—Bryan Cave

[57] ABSTRACT

This invention relates to imido-derivative peroxycarboxylic acids having the formula I:

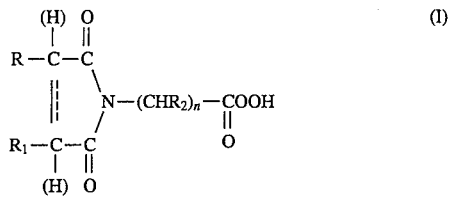

wherein R and $R_1$, which may be the same or different, represent hydrogen atoms, alkyl groups, or, taken together with the carbon atoms to which they are linked, give rise to a cyclic aliphatic ring, all of them being optionally substituted; the ... symbol indicates a simple or an olefinic bond; $R_2$ represents a hydrogen atom, an alkyl group, or an OH group, and n is an integer different from 0; the process for their preparation and their use as bleaching agents.

13 Claims, No Drawings

IMIDO-DERIVATIVE PEROXYCARBOXYLIC ACIDS

DESCRIPTION OF THE INVENTION

The present invention relates to per se new organic peroxyacids, which for brevity may be referred to as imido-derivative peroxycarboxylic acids, and to a process for their preparation.

More particularly, the present invention relates to imido-derivative peroxycarboxylic acids having the formula (I):

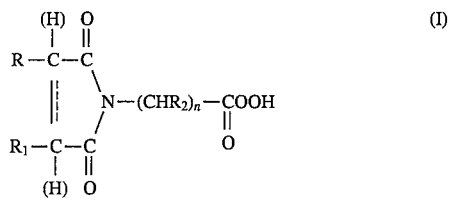

wherein:

R and $R_1$, which may be the same or different, represent hydrogen atoms, alkyl groups, or, taken together with the carbon atoms to which they are linked give rise to an aliphatic cyclic ring, all of them being optionally substituted by groups inert under the preparation conditions;

... symbol means a simple or an olefinic bond;

$R_2$ represents a hydrogen atom, an alkyl group, or an OH group; and n is an integer different from 0.

The imido-derivative peroxycarboxylic acids having the formula (I) are per se novel, and constitute a new class of compounds that are highly interesting from an industrial viewpoint.

They may, in fact, find a general use, similarly to that already known for other peroxyacids, in the field of plastics, as polymerization starter agents or initiators or as oxidizing agents for olefin epoxidation, and in many other oxidative processes in the field of fine chemicals.

More specifically, for example, the imido-derivative peroxycarboxylic acids having the formula (I) find a particularly effective application in the field of bleaching in the detergent industry.

From this point of view, generally speaking, in the past years organic peroxyacids aroused an increasing interest in the industrial field, especially as regards their excellent possibilities for use as bleaching agents in formulations for medium-low temperature washing, and even more widespreadly due to energy-saving considerations.

A large number of organic peroxyacid compounds have been described, endowed with the requisites of bleaching activity, and, in particular, of thermal stability and storage stability or shelf life, these latter requisites of course being essential for industrial-scale operations and for a widespread application of such compounds.

Therefore, many either mono- or di-peroxycarboxylic, aliphatic, straight or cyclic, or aromatic organic peroxyacids are already known and used, among others, in the field of detergents.

Previously described peroxycarboxylic acids are, e.g., diperoxydodecanedioic acid, monoperoxyphthalic acid, diperazelaic acid, substituted diperoxyglutaric and adipic acids, etc.

Therefore, an object of the present invention is to provide as per se novel compounds, the imido-derivative peroxycarboxylic acids having the above formula (I).

Another object of the present invention is to provide a simple and cheap process for the preparation of the above imido-derivative peroxycarboxylic acids having the formula (I).

A further object of the present invention is the use of imido-derivative peroxycarboxylic acids having the above formula (I) as bleaching agents in detergent formulations, and especially those intended for low-medium temperature use.

These, and still other objects of the invention which will become even clearer for those skilled in the art from the following detailed description, are achieved, according to the present invention, by providing imido-derivative peroxycarboxylic acids having the above formula (I), and by the relevant preparation process, characterized in that a substrate selected from an imido-derivative carboxylic acid having a structure corresponding to the desired imido-derivative peroxycarboxylic acids having formula (I), is reacted with concentrated $H_2O_2$, by operating in an acid reaction medium selected from concentrated $H_2SO_4$ and $CH_3SO_3H$, and in that the imido-derivative peroxycarboxylic acid (I) is then separated from the reaction mixture by per se known methods, and then washed and dried.

With reference to the above formula (I), R and $R_1$, the same or different, represent hydrogen atoms or linear or branched alkyl groups containing from 1 to 12 carbon atoms; moreover, R and $R_1$, taken together with the carbon atoms to which they are linked, may give rise to a cycloaliphatic ring containing from 4 to 12 carbon atoms, and preferably from 5 to 6 carbon atoms.

$R_2$ represents a hydrogen atom or an OH group, or a straight or branched alkyl group preferably containing from 1 to 5 carbon atoms.

Preferably, $R_2$ is a hydrogen atom.

Finally, n represents an integer different from 0, and preferably between 1 and 10.

Moreover, the R, $R_1$ and $(CHR_2)_n$ groups may in turn be substituted with one or more groups, either the same or different, inert under the reaction conditions under which the preparation takes place, and preferably selected from among $C_1$-$C_5$ alkoxy groups, hydroxy groups, nitro radicals, F, Cl, and so forth.

Imido-derivative peroxyacids having the above formula (I) which may be obtained according to the present invention, are, to name a few, 4-succinimido perbutyric acid, 3-succinimido perpropionic acid, succinimido peracetic acid, 4-cis-hexahydrophthalimido perbutyric acid, 3-cis-hexahydro-phthalimido perpropionic acid, 2-cis-hexahydrophthalimido-3-methyl perbutyric acid, 2-cis-hexahydro-phthalimido perpropionic acid, 4-(3,4,5,6-tetrahydrophthalimido) perbutyric acid, and so forth.

The substrates used as the starting material are per se known compounds and/or can be prepared according to conventional techniques.

Suitable starting substrates for obtaining the corresponding imido-derivative peroxycarboxylic acids having the formula (I) are, for exemplary purposes: 4-cis-succinimido-butyric acid, 3-cis-succinimido-propionic acid, succinimido-acetic acid, 4-cis-hexahydrophthalimido-butyric acid, 3-cis-hexahydrophthalimido propionic acid, 2-cis-hexahydrophthalimido- 3-methyl-butyric acid, 2-cis-hexahydrophthalimido-propionic acid, 4-(3,4,5,6-tetrahydrophthalimido) butyric acid, and so forth.

According to a preferred operating mode, the peroxycarboxylation reaction of the imido-derivative carboxylic acids used as the starting substrates is carried out by gradually adding, under stirring, $H_2O_2$ having a concentration within the range of from approximately 70% to approximately 90% by weight, to a solution of the substrate in concentrated $H_2SO_4$ or $CH_3SO_3H$, and by maintaining the reaction temperature throughout the reaction within the range of from 0° to 15° C.

The amount of $H_2SO_4$ or of $CH_3SO_3H$, determined at a concentration of 100%, is at least equal to 3 moles, and is preferably between about 3 and 20 moles, per mole of substrate.

The hydrogen peroxide is used in an amount which is in excess with respect to the substrate, and is at least equal to 1.2 moles per mole of substrate, and preferably between 1.5 and 6 moles per mole of substrate.

The reaction time depends on the nature of the substrate, on the operating temperature, and on the total $H_2SO_4/H_2O$ or $CH_3SO_3H/H_2O$ molar ratio present at the end of the reaction. Said ratio is maintained at least equal to 1, and preferably between approximately 1.2 and 5, by adjusting the various parameters.

The reaction time is approximately 2 hours.

The separation of the imido-derivative peroxyacid of formula (I) is carried out according to per se conventional methods, such as by filtering out the solid precipitate, by extraction with solvent, etc.

The imido-derivative peroxycarboxylic acid products having the formula (I) are usually solid at room temperature.

According to the present invention, they are especially useful in formulations of detergent compositions, e.g. granular formulations, or as bleaching agents in solution for use over a wide temperature range, e.g. between 20° and 90° C.

Therefore, the imido-derivative peroxyacids of the present invention may be used as bleaching agents directly alone, i.e., not included in a detergent composition, or, preferably, together with and incorporated into otherwise conventional detergent compositions, and containing other components and/or additives, such as, for example, builders, surfactants, soaps, zeolites, hydrotropic agents, corrosion inhibitors, enzymes, optical bleaches, stabilizing agents, other bleaching compounds, etc., etc.

Preferably, the operating temperature is between room temperature and approximately 65° C.

The preparation and use of the compositions as well as their general formulations are those known and/or are usual in the art.

The imido-aromatic peroxyacids of the present invention may be used in combination with solid or liquid detergent compositions, and/or in the presence of other bleaching peroxydic compounds.

Moreover, the imido-derivative peroxycarboxylic acids of formula (I) may be subjected to a per se well known phlegmatization process.

EXAMPLES

The present invention is disclosed in still further detail in the following examples, which are supplied for purely illustrative and not limiting purposes.

The products prepared in the examples were characterized by elemental analysis, by determining their content of active oxygen (by iodometric titration), and by using Fourier Transform Infrared Spectroscopy (FT-IR).

Example 1

20 g (0.196 mole) of $H_2SO_4$ at 96% were charged into a beaker equipped with stirrer, thermometer, and outer bath.

4.9 g (0.1009 mole) of $H_2O_2$ at 70% and 8.5 g (0.0459 mole) of 4-succinimido-butyric acid were slowly added under stirring by maintaining the internal temperature between 0° and +5° C.

The reaction was continued for 2 hours at +15° C.

At the end, the reaction mixture was then poured into 100 ml of $(NH_4)_2SO_4$ at 40% maintained under stirring at +5° C.

The resulting mixture was extracted with $CH_2Cl_2$ (6×50 ml). This extract was then washed with 30 ml of $(NH_4)2SO_4$ at 40% and finally was dried on anhydrous $Na_2SO_4$, filtered and evaporated.

7.3 g of practically pure crystalline 4-succinimido-perbutyric acid were obtained. Yield: 80%.

Elemental Analysis:

Computed for $C_8H_{11}O_5N$: C: 47.76%; H: 5.51%; N: 6.96%; O (active): 7.95%

Found C: 48.2%; H: 5.58%; N: 6.89%; O (active): 7.93%.

Melting Point 92° C. (with decomposition).

Example 2

The operating procedures of Example 1 were followed, by using 7.3 g (0.0715 mole) of sulphuric acid at 96%, 1.5 g (0.0375 mole) of $H_2O_2$ at 85%, and 3.3 g (0.0193 mole) of 3-succinimido propionic acid.

After two hours of stirring at +15° C., the reaction product was poured into 70 ml of $(NH_4)2SO_4$ at 40% maintained under stirring at +5° C. The resulting mixture was then extracted with ethyl acetate (8×40 ml) and the procedure of Example 1 was followed.

After solvent evaporation, an oily product was obtained which was dissolved in ethyl acetate and precipitated as a solid with petroleum ether, by maintaining the mixture under stirring up to complete solidification.

3 g of substantially pure 3-succinimido perpropionic acid were separated by filtration. Yield: 83%.

Elemental Analysis:

Computed for $C_7H_9NO_5$; C: 44.92%; H: 5.84%; N: 7.48%; O (active): 8.55%

Found C: 45.1%; H: 4.98%; N: 7.45%; O (active): 8.50%.

Melting Point: 78° C. (with decomposition).

Example 3

The operating procedures of Example 1 were followed by using 5.2 g (0.0509 mole) of $H_2SO_4$ at 96%, 1.5 g (0.0375 mole) of $H_2O_2$ at 85%, and 2 g (0.0127 mole) of succinimidoacetic acid.

After 2 hours of stirring at +15° C., dilution into 30 ml of $(NH_4)_2SO_4$ at 40%, extraction with ethyl acetate (4×30 ml), and evaporation of the solvent, a solid product was separated which was recrystallized by dissolving it in ethyl acetate and reprecipitating it with petroleum ether.

1.3 g of a crystalline substantially pure succinimidoperacetic acid were obtained. Yield: 60%.

Elemental Analysis:

Computed for $C_6H_7NO_5$; C: 41.62%; H: 4.07%; N: 8.09%; O (active): 9.24%

Found C: 41.95%; H: 4.10%; N: 8.06%; O (active): 9.23%.

The product started to decompose at 83° C. and was completely melted at 107° C.

Example 4

The operating procedures of Example 1 were followed, by using 3.6 g (0.0352 mole) of $H_2SO_4$ at 96%, 0.8 g (0.02 mole) of $H_2O_2$ at 85%, and 1.7 g of 4-cis-hexahydrophthalimido butyric acid.

After two hours of stirring at +15° C., dilution at +5° C. into 30 ml of $(NH_4)_2SO_4$ at 40%, extraction with ethyl acetate (3×40 ml), and evaporation of the solvent, 1.6 g of an oily product were separated, which was not crystallizable and had an active oxygen content of 6.2% (the theorical content of 4-cis-hexahydrophthalimido perbutyric acid is 6.26%). Yield: 88%.

Elemental Analysis:

Computed for $C_{12}H_{17}NO_5$; C: 56.46%; H: 6.71%; N: 5.48%; O (active): 6.26%

Found C: 56.76%; H: 6.92%; N: 5.41%; O (active): 6.20%.

The product decomposed at 32° C.

Example 5

By operating according to the process conditions of Example 1, 18 g (0.176 mole) of $H_2SO_4$ at 96%, 4 g (0.1 mole) of $H_2O_2$ at 85%, and 8 g of 3-cis-hexahydrophthalimido propionic acid were used under the same process conditions.

After 2 hours of stirring at +15° C., subsequent dilution at +5° C. into 100ml of $(NH_4)_2SO_4$ at 40%, successive extraction with ethyl ether (3×50 ml), and evaporation of the solvent, a solid product was separated which was purified by dissolving it into ethyl ether and reprecipitating it with petroleum ether.

7 g of crystalline substantially pure cis-hexadydrophthalimido perpropionic acid were obtained. Yield: 82%.

Elemental Analysis:

Computed for $C_{11}H_{15}NO_5$; C: 54.76%; H: 6.26%; N: 5.80%; O (active): 6.63%

Found C: 55.2%; H: 6.37%; N: 5.73%; O (active): 6.60%.

Melting Point: 55° C. (with decomposition).

Example 6

By operating according to the process conditions of Example 1, 23.6 g (0.231 mole) of $H_2SO_4$ at 96%, 6.8 g (0.14 mole) of $H_2O_2$ at 70%, and 11.8 g (0.0466 mole) of 2-cis-hexahydrophthalimido- 3-methylbutyric acid were used under the same process conditions.

After 2 hours of stirring at +15° C. dilution into 100 ml of $(NH_4)_2SO_4$ at 40% at a temperature of +5° C. extraction with ethyl ether (3×60 ml), and evaporation of the solvent, an oily product was separated which was dissolved in ethyl ether and precipitated as a solid with petroleum ether.

7.8 g of 2-cis-hexahydrophthalimido-3-methyl perbutyric acid 98.7% pure were obtained. Yield: 61%.

Elemental Analysis:

Computed for $C_{13}H_{19}NO_5$; C: 57.98%; H: 7.11%; N: 5.20%; O (active): 5.94%

Found C: 57.74; H: 7.14%; N: 5.17%; O (active): 5.86%.

Melting Point: 92° C. (with decomposition).

Example 7

The same process conditions of Example 1 were followed, by using 1.6 g (0.04 mole) of $H_2O_2$ at 85% and 3 g (0.0133 mole) of 2-cis-hexahydrophthalimido propionic acid.

After 2 hours of stirring at +15° C., subsequent dilution into 40 ml of $(NH_4)_2SO_4$ at 40% maintained under stirring at +5° C., and subsequent extraction with ethyl ether (3×40 ml) and evaporation of the solvent, an oily product was separated which was dissolved in $CH_2Cl_2$ and precipitated as a solid with petroleum ether.

The product was crystallized by ethyl acetate/petroleum ether to obtain 1.8 g of crystalline, 98% pure 2-cis-hexahydrophthalimido perpropionic acid. Yield: 55%

Elemental Analysis:

Computed for $C_{11}H_{15}NO_5$; C: 54.76%; H: 6.26%; N: 5.80%; O (active): 6.63%

Found C: 54.51%; H: 6.53%; N: 5.79%; O (active): 6.49%.

Melting Point: 77° C. (with decomposition).

Example 8

2 g (0.0084 mole) of 4-(3,4,5,6-tetrahydrophthalimido) butyric acid were dissolved at room temperature in 5.2 g of methanesulphonic acid.

0.7 g (0.0175 mole) of $H_2O_2$ at 85% were added to the solution maintained under stirring at +10° C., in such a way that the temperature did not exceed +15° C.

The reaction was continued for 2 hours at +15° C.

The reaction product was poured into 20 ml of $(NH_4)_2SO_4$ at 40%, maintained under stirring at +5° C., and the resulting mixture was extracted with ethyl ether (2×30 ml).

The ether extract was washed with 20 ml of $(NH_4)_2SO_4$ at 40%, then dried with anhydrous $Na_2SO_4$, filtered and evaporated.

A dense oily residue was obtained which, redissolved in ethyl ether, was precipitated as a solid with petroleum ether.

1.5 g of substantially pure 4-(3,4,5,6-tetrahydrophthalimido) perbutyric acid were separated by filtration. Yield: 70%.

Elemental Analysis:

Computed for $C_{12}H_{15}NO_5$; C: 56.91%; H: 5.97%; N: 5.53%; O (active): 6.32%

Found C: 56.65%; H: 5.90%; N: 5.47%; O (active): 6.31%.

The melting temperature of the product was between 42° and 54° C. with decomposition.

Example 9

Bleaching with 4-succinimido perbutyric acid

Bleaching tests were carried out with a detergent formulation containing 4-succinimidoperbutyric acid composition A in the amount reported in the following Table 1, as compared to a similar formulation containing, as bleaching agent, H 48 peracid (Mg salt of monoperphthalic acid, a commercially known peroxyacid, manufactured by INTEROX Chemical Ltd. London, U.K. to be used in the detergent art) (composition B).

Compositions A and B were obtained by dry blending of a detergent base, common for all the compositions, which will be better defined hereinafter, with the above listed bleaching agents. As detergent base, a granular composition was used containing all the conventional components of a detergent for washing machines (surfactants, builders and so forth), except the chemical bleaching agents, and obtained by atomization of the component mixture.

The detergent base used had the following composition:

|  | Weight % |
| --- | --- |
| Total surfactants | 15.4 |
| Sodium alkyl ($C_{12}$) benzenesulphonate, soap, ethoxylated (EO) alcohol ($C_{16}$–$C_{18}$) |  |
| Total sodium phosphates | 8.8 |
| Zeolite A | 19.8 |
| Silicate ($SiO_2/Na_2O = 2$) | 4.4 |
| Sodium sulphate | 36.6 |
| Sodium carbonate | 6.6 |
| Carboxymethylcellulose | 1.1 |
| Anti-incrusting copolymers | 4.8 |
| Water | 2.2 |
| Optical bleaching agents | 0.3 |

The metering of the compositions A and B was carried out in such a way as to introduce into the washing machine a constant amount of detergent base corresponding to 120 g and such an amount of bleaching agent as to introduce into the washing machine a quantity of total initial active oxygen equal to about 2 g of oxygen for each washing cycle, equal in all the operations.

Therefore the proportions of the compositions A and B, as reported in the following Table I, were used in the bleaching tests.

TABLE 1

| Composition A | |
| --- | --- |
| Detergent base | 120 g |
| 4-succinimidoperbutyric acid having 7.7% of active oxygen | 26 g |
| Composition B | |
| Detergent base | 120 g |
| H 48 having 5.5% of active oxygen | 39 g |

The tests were carried out with a commercial IGNIS Mod. 644 washing machine by introducing into the machine two cotton specimens 15 cm×15 cm stained with standard stains of red wine at EMPA INSTITUTE of St. Gallo (Switzerland) and marked with the "EMPA 114" mark, together with 3 Kg of cleaned cotton wipers as ballast for each washing operation.

The washings were carried out using a conventional program at low temperature (about 40° C.). The normal water of pipeline network was used, having a hardness of 14° F.

The results of the tests are reported in the following Table 2, wherein the data are expressed as bleaching %, defined as:

$$\text{Bleaching \%} = \frac{A - B}{C - B} \times 100$$

wherein:

A=degree of whiteness (%) of the specimen bleached after the test;

B=degree of whiteness (%) of the specimen before the test;

C=degree of whiteness (%) of the completely bleached specimen and wherein the degrees of whiteness were measured by means of an Elrepho Zeiss reflectometer, assuming MgO=100% of whiteness, and using filter N. 6 (=464 nm).

TABLE 2

|  | Bleaching % |
| --- | --- |
| Composition A | 58 |
| Composition B | 52 |

The data show the higher bleaching power of the claimed peroxyacid in comparison with that of H 48.

EXAMPLE 10

(Application example)

Bleaching tests were carried out with the novel imido-derivative peroxyacid listed in the annexed Tables 3 and 4, at an alkaline pH (Table 3) and an acid pH (Table 4), as compared to H 48 (Mg salt of monoperphthalic acid), a commercial peroxyacid known in the detergent art, and manufactured by INTEROX Chemical Ltd., London, U.K. (Tables 3 and 4).

All tests were carried out at constant temperature of 40° C. and 60° C. with an initial concentration of total active oxygen in the bleaching solution equal for all products, and equal to 200 mg/l.

Process:

For each test, 500 ml of deionized water in a 1,000 ml flask equipped with a condenser, was heated to a temperature of 40° or 60° C. and adjusted to a pH value of 9.5 (with NaOH) (Table 3) and to a pH 3–4 (corresponding to the pH value which may be obtained by the direct dissolution of the subject peroxyacids) (Table 4); then the bleaching product was added with stirring with such amounts thereof as shown in the following Tables, and immediately thereafter, two cotton specimens of 10 cm×10 cm stained with standard stains of red wine at EMPA INSTITUTE of St. Gallen (Switzerland), and marked with the "EMPA 114" mark, were added.

The system was subsequently kept stirring for 60 minutes and, at the end of this time, the specimens, rinsed under running water, were dried and ironed, and were then subjected to an evaluation of the bleaching effect by means of measurements of degree of whiteness by reflectomerry. The results are reported in the following Tables 3 and 4, wherein the data are expressed as bleaching %, as described in Example 9.

The data listed in Table 3, which are tests carried out at an alkaline pH at 60° C., show that the bleaching power of the peroxyacids of the present invention is equal to or higher than that of H 48 product and it is very much higher than that of H 48 when the washing is carried out at low temperatures (40° C.).

Likewise, the data listed in Table 4 (which refer to tests carried out at 60° C.) show that the peroxyacids of the present invention, in acid solution, have a bleaching power particularly high (this is particularly surprising in consideration of the fact that the peroxidic compounds generally show a bleaching activity that is very modest in this condition) and very much higher than that of H 48.

TABLE 3

Tests Carried out at Alkaline pH (9.5)

| Compound | Amounts used in the tests (grams) | Initial concentration of total active oxygen (mg/l) | Bleaching % at 40° C. | at 60° C. |
| --- | --- | --- | --- | --- |
| 4-succinimido-perbutyric acid (Ex. 1) (Active oxygen: 7.9%) | 1.27 | 200 | 74 | 82 |
| 3-succinimido-perpropionic acid (Ex. 2) (Active oxygen: 8.5%) | 1.22 | 200 | 76 | 80 |
| 2-cis-hexahydro-phthalimido-3-methyl-perbutyric acid (Ex. 6) (Active oxygen: 5.8%) | 1.73 | 200 | — | 81 |
| H 48 (Active oxygen: 5.5%) | 1.86 | 200 | 67 | 80 |

TABLE 4

Tests Carried out at Acid pH (3–4)

| Compound | Amounts used in the tests (grams) | Initial concentration of total active oxygen (mg/l) | Bleaching (%) |
| --- | --- | --- | --- |
| Example 1 (Active oxygen 7.9%) | 1.27 | 200 | 76 |
| Example 2 (Active oxygen 8.5%) | 1.22 | 200 | 76 |
| Example 6 (Active oxygen 5.8%) | 1.73 | 200 | 79 |
| H 48 (title = 5.5%) | 1.86 | 200 | 60 |

What is claimed is:

1. Imido-alkyl-per-carboxylic acids having formula (I):

$$\begin{array}{c}(H) \quad O \\ | \quad \| \\ R-C-C \\ \| \quad \diagdown \\ \quad\quad N-(CHR_2)_n-C-O-OH \\ \| \quad \diagup \quad\quad\quad \| \\ R_1-C-C \quad\quad\quad\quad O \\ | \quad \| \\ (H) \quad O \end{array} \quad (I)$$

wherein:

R and $R_1$, which may be the same or different, represent H, a linear or branched alkyl group, having from 1 to 12 C atoms, optionally bearing at least one substituent group, which may be the same or different from each other, selected from F, Cl, OH, $NO_2$ and $C_1$–$C_5$ alkoxy; or R and $R_1$ give rise, along with the two adjacent C atoms, to a cycloaliphatic ring having from 4 to 6 C atoms;

the symbol . . . represents a single or a double bond;

n is an integer from 1 to 10;

$R_2$ represents H, OH or a linear or branched alkyl group having from 1 to 5 carbon atoms, optionally bearing at least one of the substituent groups listed for R or $R_1$.

2. Hexahydro-, or tetrahydro-, phthalimido-alkyl-percarboxylic acids having formula (II) or (III):

$$\text{(II)}$$

$$\text{(III)}$$

wherein $R_2$ and n have the same meaning as in claim 1.

3. A bleaching composition comprising an imidoderivative peroxycarboxylic acid of the formula $$\begin{array}{c}(H) \quad O \\ | \quad \| \\ R \\ \vdots \quad\quad N-(CHR_2)_n-C-O-OH \\ \vdots \quad\quad\quad\quad\quad\quad \| \\ R_1 \quad\quad\quad\quad\quad\quad O \\ | \\ (H) \quad O \end{array} \quad (I)$$

wherein:

R and $R_1$, which may be the same or different, represent H, a linear or branched alkyl group having from 1 to 12 carbon atoms, optionally bearing at least one substituent group which may be the same or different and being selected from the group consisting of F, Cl, OH, $NO_2$ and $C_1$–$C_5$ alkoxy, or R and $R_1$ together with the two adjacent carbon atoms define a cycloaliphatic ring having from 4 to 6 carbon atoms;

the symbol - - - represents a single or a double bond;

n is an integer from 1 to 10; and $R_2$ represents H, OH or a linear or branched alkyl group having from 1 to 5 carbon atoms, optionally bearing at least one of the substituent groups listed for R or $R_1$.

4. The composition of claim 3 further comprising a detergent.

5. The composition of claim 4 additionally containing an additive selected from the group consisting of a builder, a surfactant, a soap, a zeolite, a hydrotropic agent, a corrosion inhibitor, an enzyme, and mixtures thereof.

6. A compound which is 4-succinimido-perbutyric acid.

7. A compound which is 3-succinimido-perpropionic acid.

8. A compound which is succinimido-peracetic acid.

9. A compound which is 4-hexahydrophthalimido-perbutyric acid.

10. A compound which is 3-hexahydrophthalimido-perpropionic acid.

11. A compound which is 2-hexahydrophthalimido-3-methyl-perbutyric acid.

12. A compound which is 2-hexahydrophthalimido-perpropionic acid.

13. A compound which is 4-(3,4,5,6-tetrahydrophthalimido) perbutyric acid.

* * * * *